(12) United States Patent
Han et al.

(10) Patent No.: US 6,858,403 B2
(45) Date of Patent: Feb. 22, 2005

(54) POLYMER MATRIX CONTAINING CATALASE CO-IMMOBILIZED WITH ANALYTIC ENZYME THAT GENERATES HYDROGEN PEROXIDE

(75) Inventors: In Suk Han, Salt Lake City, UT (US); Dal-Young Jung, Salt Lake City, UT (US)

(73) Assignee: M-Biotech, Inc., Sandy, UT (US)

( * ) Notice: Subject to any disclaimer, the term of this patent is extended or adjusted under 35 U.S.C. 154(b) by 127 days.

(21) Appl. No.: 09/824,552

(22) Filed: Apr. 2, 2001

(65) Prior Publication Data

US 2002/0006634 A1 Jan. 17, 2002

Related U.S. Application Data

(63) Continuation-in-part of application No. 09/308,392, filed as application No. PCT/US98/20750 on Sep. 30, 1998, now Pat. No. 6,268,161.
(60) Provisional application No. 60/194,042, filed on Apr. 3, 2000.

(51) Int. Cl.[7] .............................. C12Q 1/30; C12Q 1/54; C12N 11/18; C12N 11/04; C12M 1/34
(52) U.S. Cl. .............................. 435/27; 435/14; 435/25; 435/175; 435/176; 435/180; 435/182; 435/287.1; 435/817
(58) Field of Search .................................. 435/174, 176, 435/180, 182, 817, 14, 27, 175, 287.1

(56) References Cited

U.S. PATENT DOCUMENTS

| 4,655,880 A | 4/1987 | Liu ............................ 264/1 T |
| 5,141,873 A | 8/1992 | Steudle et al. .............. 436/148 |
| 5,431,160 A | 7/1995 | Wilkins ....................... 128/635 |
| 5,665,065 A | 9/1997 | Colman et al. ............... 604/66 |
| 5,967,975 A | 10/1999 | Ridgeway .................... 600/300 |
| 6,102,856 A | 8/2000 | Groff et al. ................. 600/301 |
| 6,113,539 A | 9/2000 | Ridenour ..................... 600/300 |
| 6,150,942 A | 11/2000 | O'Brien ................... 340/573.1 |
| 6,198,394 B1 | 3/2001 | Jacobsen et al. ......... 340/573.1 |

FOREIGN PATENT DOCUMENTS

EP         WO 99/17095         4/1999

OTHER PUBLICATIONS

Albin, G.W., "Theoretical and Experimental Studies of Glucose Sensitive Membranes," J. Controlled Release, 1987, p. 267–291, vol. 6.
Allcock, H. R., "Synthesis and Chacterization of pH–Sensitive Ploy(organophosphazene) Hydrogels," Biomaterials, 1996, p. 2295–2302, vol. 17.
Bouin, J.C., "Relative Efficiencies of a Soluble and Immobilized Two–Enzyme System of Glucose Oxidase and Catalase,:" Biochim. Biophys. Acta, 1976, p. 23–36, vol. 438.

(List continued on next page.)

*Primary Examiner*—David M. Naff
(74) *Attorney, Agent, or Firm*—Mallinckrodt & Mallinckrodt; Robert R. Mallinckrodt (57) ABSTRACT

Hydrogels containing catalase co-immobilized with an analyte-sensitive enzyme such as glucose oxidase are disclosed. The hydrogels may be pH-sensitive, and preferably are thin and lightly crosslinked. The catalase is present in concentrations ranging generally from 100 units/ml to about 1000 units/ml. These hydrogels have much faster swelling response times as compared to hydrogels without catalase, and are useful in biosensors and analyte-responsive drug delivery devices. The hydrogels also have an increased useful life, due to protection of the immobilize analyte-sensitive enzyme from degradation by hydrogen peroxide.

12 Claims, 4 Drawing Sheets

OTHER PUBLICATIONS

Bouin, J.C., "Parameters in the Construction of an Immobilized Dual Enzyme Catalyst," Biotechnol, Bioeng., p. 179–187, vol. 18.

Bronsted, H., *Polyelectrolyte Gels; Properties, Preparation and Application, AM. Chem. Soc.*, 1992, p. 285–305, Washington, D.C.

Christakis, O.M., "On the Mechanism of Immobilized Glucose Oxidase Deactivation by Hydrogel Peroxide," Biotechnol. Bioengin., 1982, p. 2419–2439, vol. 21.

Ghandehari, H., "Biodegradable and pH Sensitive Hydrogels: Synthesis by a Polymer–Polymer Reaction," J. Macrol. Chem. Phys., 1996, p. 197–980. vol. 197.

Gough, D.A. and Lucisano, "Transient Response of the Two–Dimensional Glucose Sensor," J. Anal. Chem., 1998, p. 1272–1281, vol. 60.

Gough, D.A., "Two–Dimensional Enzyme Electrode Sensor for Glucose," Anal. Chem., 1985, p. 2351–2357, vol. 57.

Gough, D.A., "Progress Toward a Potentially Implantable, Enzyme–Based Glucose Sensor," Diabetes Care, 1982, p. 190–198, vol. 5.

Ishiara, L., "Glucose Induced Permeation Control of Insulin through a Complex Membrane Consisting of Immobilized Glucose Oxidase and Poly(amino)," Polym. J., 1984, p. 625–631, vol. 16.

Ishihara, K., "Control of Insulin Permeation through a Polymer through a Polymer Membrane With Responsive Function for Glucose," Makrol. Chem. Rapid Commun., 1983, p. 327–331, vol. 4.

Ito, Y., "An Insulin–Releasing System that is Responsive to Glucose," J. Controlled Release, 1989, p. 195–203, vol. 10.

Jung, D.Y., "Catalase Effects on Glucose–Sensitive Hydrogels," Macrol., 2000, p. 3332–3336, vol. 9.

Kim, S.W., "Hydrogels: Swelling, Drug Loading, and Release," Phar. Res., 1992, p. 283–290, vol. 9.

Klumb. L.A., "Design of Insulin Delivery Devices Based on Glucose Sensitive Membranes," J. Controlled Release, 1992, p. 59–79, vol. 18.

Kost, J., "Glucose–Sensitive Membranes Containing Glucose Oxidase: Activity, Swelling and Permeability Studies," Biomed. Mater. Res., 1985, p. 1117–1133, vol. 19.

Krysteva, M.A., "Multienzyme Membranes for Biosensors," J. Chem. Tech, Biotech., 1992, p. 13–18, vol. 54.

Owusu, R.K., "Flow Microcalorimetric Study of Immobilized Enzyme Kinetics Using the Co–Immobilized Glucose Oxidase–Catalase System," Biochim. Biophys. Acta, 1986, p. 83–91, vol. 872.

Philippova, O., "pH–Responsive Gels of Hydrophobically Modified Poly(acrylic acid)," Macrol., 1997, p. 8278–8285, vol. 30.

Prenosil, J.E., "Immobilized Glucose Oxidase–Catalase and Their Deactivation in a Differential–Bed Loop Reactor," Biotechnol. Bioeng., 1979, p. 89–109, vol. 21.

Rao, J.K., "Implantable Controlled Delivery System for Proteins Based on Collagen–pHEMA Hydrogels," Biomaterials, 1994, p. 383–389, vol. 16.

Reach, G., "Can Continuous Glucose Monitoring Be Used for the Treatment of Diabetes," Anal. Chem., 1992, p. 381–386, vol. 64.

Sato, S., "Self-Regulating Insulin Delivery Systems," J. Controlled Release, 1984, p. 67–77, vol. 1.

Schott, H., "Kinetics of Swelling of Polymers and Their Gels," J. Pharm Sci., 1992, p. 467–470, vol. 81.

Serres, A., "Temperature and pH–Sensitive Polymers for Human Calcitonin Delivery," Pharm. Res., 1996, p. 196–201, vol. 13.

Siegel, R.A., "pH–Dependent Equilibrium Swelling Properties of Hydrophobic Polyelectrolyte Copolymer Gels," Macromolecules, 1988, p. 3254–3259, vol. 21.

Teijon, J.M., "Cytarabine Trapping in Poly(2 hydroxyethyl methacrylate) Hydrogels: Drugs Delivery Studies" Biomaterials, 1997, p. 383–388, vol. 18.

Vakkalanka, S.K., "Temperature–and pH–sensitive Terpolymers for Modulated Delivery of Streptokinase," J. Biomater. Poly. Sci., 1996, p. 119–129, ed. 8.

Wasserman, B.P., "High–Yield Method for Immobilization of Enzymes," Biotechnol. Bioeng., 1980, p. 271–287, vol. 22.

Wilkins, E.S., "Towards Implantable Glucose Sensors: A Review," J. Biomed. Eng., 1989, p. 354–361, vol. 11.

Wingard, Jr., L. B., "Immobilized Enzyme Electrodes for the Potentiometric Measurement of Glucose Concentration: Immobilization Techniques and Materials," J. Biomed. Mater. Res., 1979, p. 921–935, vol. 13.

POLYMER MATRIX CONTAINING CATALASE CO-IMMOBILIZED WITH ANALYTIC ENZYME THAT GENERATES HYDROGEN PEROXIDE

This application for a utility patent is a continuation in part of U.S. patent application Ser. No. 09/308,392, filed May 11, 1999, now U.S. Pat. No. 6,268,161, which is a 371 of PCT/US98/20750, filed Sep. 30,1998, and claims the benefit of U.S. Provisional Patent Application No. 60/194, 042, filed Apr. 3, 2000.

BACKGROUND OF THE INVENTION

Field of the Invention

This invention is generally related to the use of hydrogels containing oxidoreductase enzymes in biosensors and controlled drug delivery systems, and more particularly to the inclusion of catalase in such biosensors and drug delivery systems.

DESCRIPTION OF RELATED ART

The current growth of hydrogel applications in drug delivery and biosensors is ascribed in part to the biocompatibility of hydrogels, and in part to fast and reversible volume changes in response to external stimuli such as temperature, pH, electric and magnetic fields, or analyte concentration. Thus these hydrogels are sometimes called "stimulus responsive polymers". (Gehrke S H. 1993 Adv. Polym. Sci. 110:82)

The swelling and shrinking of stimulus responsive polymers has been successfully used to control drug release in several systems: see for example Kost J et al 1985 Biomed Mater. Res. 19:1117; Teijon J M et al 1997 Biomaterials 18:383; Sato S et al J. 1984 Controlled. Release 1:67; Kim S W et al 1992 Pharm. Res. 9:283 Serres A et al 1996 Pharm. Res. 13:196; Ishihara K et al 1983 Makromol. Chem. Rapid Conmmun. 4:327; Ghandehari H et al 1996 J. Macromol. Chem. Phys. 197:965; Chen L L 1998 Pharm. Dev. Technol. 3:241; Khare A R et al 1993. J. Biomater. Sci. Polym. Ed. 4:275; Schott H 1992 J. Pharm. Sci. 81:467; Allcock H R et al 1996 Biomaterials 17:2295; Vakkalanka S K et al 1996 3. Biomater. Sci. Polym. Ed. 8:119; Rao J K et al 1994 Biomaterials 15:383; Siegel R A et al 1988 Macromolecules 21:3254; Brondsted H et al Polyelectrolyte gels: Properties, Preparation, and Application, Harland R S., Prud Homme P K, eds ACS: 285, 1992; and Ishihara K et al 1984 Polym. J. 16:625, the teachings of all of which are hereby incorporated by reference.

One approach is to use pH sensitivity to mediate changes in swelling. A pH-sensitive hydrogel undergoes very large and reversible volume changes in response to pH changes within the hydrogel. Two main types of pH-sensitive hydrogels are acidic hydrogels and basic hydrogels. Acidic hydrogels by definition will be ionized and hence swollen at high pH, and uncharged and unswollen at low pH (Ghandehari H et al 1996 J. Macromol. Chem. Phys. 197:965; Brondsted H et al Polyelectrolyte gels: Properties, Preparation, and Application, Harland R S., Prud Homme P K, eds ACS: 285, 1992). Swelling behavior of a basic hydrogel has the opposite dependence on pH. The pH sensitivity is caused by pendant acidic and basic groups such as carboxylic acids, sulfonic acids, primary amines, and quaternary ammonium salts. (Ghandehari H et al 1996 J. Macromol. Chem. Phys. 197:965; Siegel RA et al 1988 Macromol. 21:3254; Brondsted H et al Polyelectrolyte gels: Properties, Preparation, and Application, Harland R S., Prud Homme P K, eds ACS: 285, 1992). Carboxylic acid groups for example are charged at high pH and uncharged at low pH, whereas the reverse is true for primary amine groups and quaternary ammonium salts.

The transition pH for a given pendant group is primarily determined by the pKa value for that pendant group, and by the hydrophobicity of nearby monomers in the polymer chain. (Brondsted, H. et al., Polyelectrolyte Gels: Properties, Preparation, and Application, Harland R S., Prud Homme P K, eds ACS: 285, 1992). Hence, one can manipulate the critical pH value at which the pH-sensitive hydrogel undergoes a volume transition by choosing pendant groups with the appropriate pKa values and by adjusting the hydrophobicity, choosing from a number of monomers such as: poly(alkyl acrylate), poly(alkylmethacrylate), poly(2-hydroxyethyl methacrylate) (pHMA), poly(2-hydroxypropylmethacrylate) (p-HPMA), poly(acrylamide), poly(N-vinyl pyrrolidone), poly(vinyl alcohol) (PVA), polyethylene oxide (PEO), and poly(etherurethane). (Kost J et al 1985 Biomed Mater. Res. 19:1117; Teijon J M et al 1997 Biomaterials 18:383; Sato S et al J. 1984 Controlled. Release 1:67; Kim S W et al 1992 Pharm. Res. 9:283; Serres A et al 1996 Pharm. Res. 13:196; Ishihara K et al 1983 Makromol. Chem. Rapid Commun. 4:327; Ghandehari H et al 1996 J. Macromol. Chem. Phys. 197:965; Chen LL 1998 Pharm. Dev. Technol. 3:241; Khare A R et al 1993. J. Biomater. Sci. Polym. Ed. 4:275; Schott H 1992 J. Pharm. Sci. 81:467; Allcock H R et at 1996 Biomaterials 17:2295; Vakkalanka S K et al 1996 J. Biomater. Sci. Polym. Ed. 8:119; Rao J K et al 1994 Biomaterials 15:383; Siegel R A et al 1988 Macromolecules 21:3254; Brondsted H et al Polyelectrolyte gels: Properties, Preparation, and Application, Harland R S., Prudhorune P K, eds ACS: 285, 1992; Ishihara K et al 1984 Polym. J. 16:625; Philippova O 1997 Macromol. 30:8278; Ito Y 1989 J. Control. Release 10:195; Wilkins E S 1989 J. Biomed. Eng. 11:354; all of whose contents are hereby incorporated by reference.). The monomers listed above can also be used in various combinations to form copolymers.

In a biosensor, the swelling and shrinking of the hydrogel is usually made to be responsive to changes in the level of a biological indicator or molecule of interest. This is generally achieved by incorporating into the hydrogel an enzyme, receptor, antibody, or other agent which binds the molecule of interest. Oxidoreductase enzymes are one category of such agents, which find particular use in biosensors. The characteristics of oxidoreductase enzymes of particular value in sensor applications is the production of oxygen by the enzyme reaction.

Among the oxidoreductase currently being investigated for use in biosensors are glucose oxidase (for sensing blood sugar levels), cholesterase (for sensing cholesterol levels), alcohol dehydrogenase (for sensing alcohol levels), and penicillinase (for sensing penicillin levels). Besides those named here, there are over 100 known oxidoreductase enzymes, and at least some of these are likely to find future use in biosensors.

A pH-sensitive hydrogel containing glucose oxidase (GOx) enzyme is called a glucose-sensitive hydrogel (GSH) due to its responsiveness to environmental glucose concentrations. Thermally stable GOx is a flavin-containing glycoprotein which catalyzes a reaction which is very specific for glucose, and which produces gluconic acid and hydrogen peroxide in the presence of glucose and oxygen as shown below. Therefore, increases in the environmental glucose concentration lower the pH value within the GSH.

Several attempts have been made to utilize this catalytic reaction in glucose biosensors. (Wilkins, E. S., J. Biomed. Eng. 11:354, 1989; Gough, D. A. et al., Diabetes Care, 5:190, 1982; Gough, D. A. et al., Anal. Chem. 60:1272, 1988; Gough, D. A. et al., Anal. Chem. 57:2351, 1985).

Glucose biosensors based on amperometric methods are the most highly developed. In the amperometric method, an electrode is used which produces a current proportional to the diffusional flux of hydrogen peroxide to the electrode surface, or, alternatively, proportional to the diffusional flux of oxygen to the electrode surface. (Wilkins, E. S., J. Biomed. Eng. 11:354, 1989; D. A. Gough et al., Diabetes Care 5:190, 1982; D. A. Gough et al. Anal. Chem. 60:1272, 1988; Gough et al., Anal. Chem.57:2351, 1985). At steady state, the diffusional flux of hydrogen peroxide to the electrode surface equals the rate at which hydrogen peroxide is produced by the GOx reaction in the hydrogel adjacent to the electrode. However, unlike the hydrogels considered here, the hydrogels in amperometric glucose biosensors do not swell in response to pH changes.

An important physical property of pH-sensitive GSHs is the ability to change volume in response to changes in environmental glucose concentrations, due to changes in pH within the hydrogel caused by the reaction of the GOx enzyme. This physical phenomenon has been applied in insulin delivery devices to control insulin permeability through GSHs. (S. Sato et al., J. Controlled. Release 1:67, 1984; S. W. Kim et al., Pharm. Res. 9:283, 1992; A. Serres et al., Pharm. Res. 13:196, 1996; K. Ishihara et al., Polym. J. 16:625, 1984).

pH-sensitive glucose hydrogels are useful in devices using either amperometric means or pressure transducers to detect glucose concentrations. For such applications, two major problems with the GOx enzymatic process have been identified: insufficient oxygen supply for the reaction, and the decay of the GOx activity with time due to peroxide-induced degradation (D. A.Gough et al., Diabetes Care 5:190 1982; Gough et al., Anal. Chem. 60:1272, 1988; Gough et al., Anal. Chem. 57:2351, 1985; L. A. Klumb et al., J. Control. Release 18:59, 1992; O. M. Christakis et al., Biotechnol. Bioeng. 24:2419, 1982).

Attempts to solve the first problem, oxygen depletion, have been made by using oxygen substitutes or external oxygen reservoirs. Several groups have tried to help solve the oxygen deficit problem in glucose sensors and insulin delivery systems with a theoretical model which evaluates different possible device designs (G. Reach et al., Anal. Chem. 64:381, 1992; Gough et al. 1988; Gough et al. 1985; Klumb et al. 1992). Klumb et al. have developed a theoretical model to evaluate possible designs for a glucose-responsive insulin delivery system. They designed several insulin delivery devices with an oxygen supplying system such as an oxygen diffusion tank to improve oxygen limitation in macroporous GSHs. However, oxygen-supplying systems are cumbersome and, where pure oxygen is used, may constitute a hazard.

Both the problems mentioned above, of oxygen limitation and of peroxide-caused degradation, can be partially alleviated using the following enzymatic reaction of catalase:

The catalase reaction produces oxygen, which helps meet the oxygen requirement of the GOx enzymatic reaction. Furthermore, the removal of hydrogen peroxide has been shown to reduce peroxide-induced degradation of the GOx enzyme. (Krysteva, M. A., et al, J. Chem. Tech. Biotechnol. 54:13, 1992; Wingard Jr., L. B., et al., J. Biomed. Mater. Res. 13:921, 1979; Owusu, R. K. et al., Biochim. Biophys. Acta 872:83, 1986; Bouin, J. C. et al., Biochim. Biophys. Acta. 438:23, 1976; Waasserman, B. P. et al., Biotechnol. Bioeng. 22:271, 1980; Prenosil, J. E., Biotechnol. Bioeng. 21:89, 1979; Bouin, J. C. et al., Biotechnol. Bioeng. 18:179, 1976).

In summary, for both insulin delivery devices and glucose biosensors, GOx stability is essential for long term use in vivo. For insulin delivery devices and the pressure-based glucose biosensors, a rapid swelling kinetic is also important, to provide the best performance. However, to our knowledge, there has been no previous determination of the appropriate amounts of catalase to use in hydrogel-based sensors.

Thus, a primary objective of the present invention is to provide improved pH-sensitive hydrogels and polymers containing oxidoreductase enzymes, incorporating appropriate amounts of catalase to remove hydrogen peroxide and to produce oxygen and water in situ, thereby enhancing the swelling kinetics of the hydrogels. A further objective of the invention is to provide methods for making such improved hydrogels. A still further objective is to provide a hydrogel-based glucose biosensor having improved swelling kinetics and longer useful life.

SUMMARY OF THE INVENTION

The invention comprises a hydrogels containing an analyte-sensitive enzyme which generates hydrogen peroxide, co-immobilized with catalase, with the catalase being present in amounts ranging from about 100 units/ml to about 1000 units/ml. The term "hydrogel" is intended to encompass any polymer matrix suitable for use in hydrated conditions. In one embodiment, the analyte is glucose and the analyte-sensitive enzyme is glucose oxidase. In addition to glucose oxidase, the invention is applicable any analyte-sensitive enzyme which generates hydrogen peroxide as part of the reaction. These include monoamine oxidase as well as many oxidoreductases.

The invention further encompasses biosensors incorporating these hydrogels. The hydrogels may preferably be formulated such that swelling of the gel permits flow of a drug such as insulin out of the gel. Thus, in a further embodiment the invention encompasses analyte-responsive drug delivery devices containing hydrogels which meet the above description. The hydrogels may be used with biosensors or drug-delivery devices which use pressure transducers or amperometric means to register analyte concentration. Hydrogels according the invention may also be used with devices employing gas reservoirs or semi-permeable membranes. The invention further includes methods for using catalase in hydrogels, biosensors and analyte-responsive drug delivery devices.

DETAILED DESCRIPTION OF THE INVENTION

In one embodiment, glucose is the analyte and glucose oxidase is the analyte-sensitive enzyme. Preferably, the hydrogel for this application is relatively thin, between about 0.1 mm and 0.4 mm, and lightly crosslinked. In this embodiment, glucose oxidase (GOx) will generally be used at a concentration ranging from about 500 units/ml to 1500 units/ml, as this concentration range is suitable for measuring blood glucose levels in human beings. For GOx at these levels, the useful range of catalase concentration is from about 100 units/ml to about 1000 units/ml. The best results were achieved by about 600 units/ml; 900 units/mi did not produce improvement in swelling kinetics and in fact appeared to produce less of an improvement than 600 units/ml. It is thought that at 900 units/ml, the amount of catalase is high enough to possibly cause protein aggregation which denatures the enzyme, or by limiting substrate diffusion.

In a highly preferred embodiment, the hydrogel is selected to have properties suitable for an analyte-responsive drug delivery device. For example, in such a device using glucose oxidase, swelling of the hydrogel in response to increased glucose concentration would permit diffusion of insulin out of the gel into the bloodstream. HPMA/DMA hydrogels are known to be useful for insulin delivery in response to the concentration of glucose (Ishihara K et al., Polym. J. 16:625, 1984), and are used for the experiments presented in the Figures. However, other hydrogels and polymer matrices having suitable swelling and diffusional properties could be used.

In one highly preferred embodiment, glucose-sensitive hydrogels (GSHs) responsive to both pH value and glucose concentration are prepared by polymerizing solutions containing hydroxypropyl methacrylate, N,N-dimethylaminoethyl methacrylate, and tetraethyleneglycol dimethacrylate in the mole ratio 70:30:2. Glucose oxidase (GOx) at concentrations of between 500 units/ml and 1500 units/ml, and catalase at concentrations of from 100 units/ml to 900 units/ml are included in the pre-gel solution and become physically immobilized within the hydrogel matrix.

With respect to making of the hydrogel, Hydroxypropyl methacrylate (HPMA, Polysciences, Inc.) and N,N-dimethylaminoethyl methacrylate (DMA, Polysciences, Inc.) were vacuum distilled in the presence of polymerization inhibitor prior to use in copolymerization. tetra-ethyleneglycol dimethacrylate (TEGDMA, Polysciences, Inc.), ethyleneglycol (BG, Aldrich), N,N,N',N'-tetramethylethylenediamine (TEMED; Aldrich), ammonium persulfate (APS; Aldrich), glucose oxidase (GOD, Sigma) and catalase (Sigma) were used as obtained. Sodium dihydrogen phosphate, potassium hydrogen phosphate, TRIS HCl (ICN), TRIS Base (Sigma), KCl, and NaCl were used as received. Buffers were prepared from citric acid, Tris HCl, Tris Base, and PBS with pH adjusted with NaOH or HCl to the desired range. Measurement of pH was performed using a Corning pH meter with G-P Combo w/RJ pH probe. Calculated amounts of NaCl were added to the buffer solutions in order to adjust the ionic strength to 0.15 M, mimicing physiological conditions.

Glucose-Sensitive Hydrogel (GSH) Preparation. Each glucose-sensitve hydrogel was prepared by redox polymerization between two glass plates (10 cm×10 cm) with the gap set using a teflon spacer (0.40 mm). These slide-molds were held together by metal clamps to provide a uniform internal cavity for the pregel solutions. Each pregel solution contained HPMA, DMA, TEGDMA, EG, TEMED, and APS in the mole ratio 70:30:2:10:0.03:0.001. The concentration of these species in the solution was adjusted to insure complete monomer conversion in the final product. Calculated amounts of glucose oxidase and catalase solutions were prepared separately and added into the pregel solution. Pregel solutions were degassed by bubbling nitrogen for 10 min and/or by stirring under a rough vacuum for 5–10 min and then injected into the slide-mold. The molds were kept at 4° C. for 12–16 h to facilitate complete polymerization. The hydrogel slab was separated from the two glass plates with a razor blade and cut into a 9.0 mm by 9.0 mm square disk using a long-blade cutter. All gel disks were washed in 0.5× and 1.0× PBS at least 3 days (2–3 times a day) and then stored in 1.0× PBS buffer at 4° C. overnight or until use.

pH Swelling Studies. Hydrogel disks were immersed in 50 mM Tris buffer (pH 10) overnight or until they reached a constant weight value at room temperature (22–23° C.). The total ionic strength of each buffer at each pH was adjusted to the same value (0.15 M) with a calculated amount of NaCl. Periodically, disks were withdrawn from the buffer solution and weighed after removal of excess surface solution by light blotting with a laboratory tissue. The disk weights were individually monitored in this way until they reached a constant value. This typically required from 6 h to 24 h depending on the value of the pH and the composition of the sample, and the buffer was replaced several times to maintain a constant pH during the experiment. The relative swelling ratio (RSR) for a gel sample was calculated as RSR=[Ww–Wd]/Wd where Ww and Wd are swollen and dry disk weights, respectively. Dry weights were determined by weighing gel samples after at least ten days of drying in an oven at 60° C.

Glucose Swelling Studies. Hydrogel disks were immersed in PBS (pH 7.2) overnight or until they reached a constant weight value. A series of glucose solutions (75, 150, and 300 mg/dL) were prepared in a 100 mL bottle prior to use. The hydrogel disks were placed in the glucose solution and the temperature was controlled using a Precision Scientific Inc. dual chamber water bath and a Thermolyne 42000 Incubator. Oxygen saturation was accomplished by vigorous bubbling of oxygen through the glucose solution with constant stirring during the experimental period In certain other experiments, no oxygen bubbling was performed, and the solution was exposed to oxygen only at the air/solution interface at the top of the solution container. Periodically the sample gels were taken from the glucose bath, weighed after removing the excess buffer solution on the surface, and then replaced in the bath. The relative swelling ratio for a gel sample was calculated as RSR=[W(t)–Wd]/Wd where W(t) and Wd are sample weights at time t and dry weights, respectively.

Figure 1:
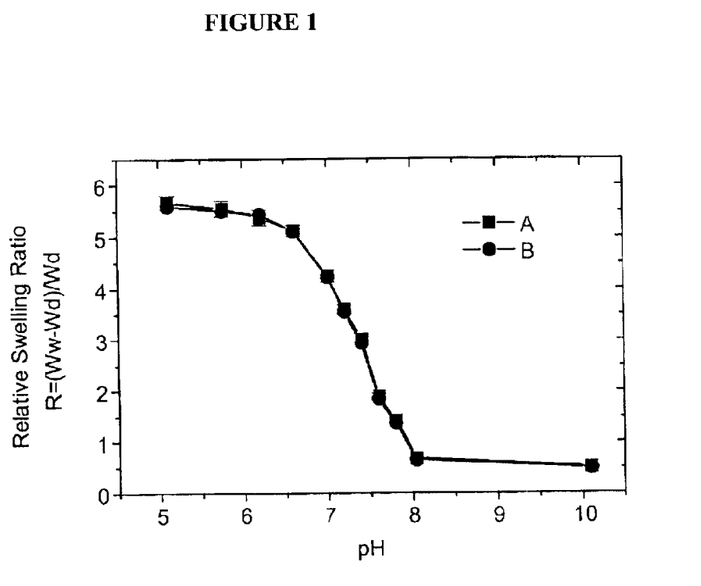
FIG. 1 depicts the equilibrium degree of swelling as a function of pH at fixed ionic strength, for a hydroxypropyl methacrylatel N,N-dimethylaminoethyl methacrylatel tetra-ethyleneglycol dimethacrylate (HPMA/DMA/TEGDMA) (70:30:2 mol ratio) hydrogel of dimensions 0.9 mm×0.9 mm×0.4 mm, containing a fixed concentration of GOx of 1000 unit/ml of pre-gel solution. Curve A is the profile with 600 unit/ml incorporated catalase; curve B is for the hydrogel with no catalase. Swelling was measured in solutions of varyious pHs, in a 50 mM Tris buffer at fixed ionic strength of 0.15 M and at room temperature. The hydrogel was incubated for 48 hours at each pH. Relative ratio=(hydrogel weight at a pH—dried hydrogel weight)/dried hydrogel weight. (n=3)

In the HPMA/DMA hydrogel, the basic pendant group, a tertiary amine on DMA, becomes charged at low pH, thereby swelling the hydrogel (FIG. 1). The swelling response is most sensitive at a pH close to the pKa value of the ionizable group of the hydrogel. (Brondsted, H. et al., in: Polyelectrolyte Gels: *Properties, Preparation, and Application*, Harland, R. S. and Prudhomme, P. K., eds. American Chemical Society, Washington, D.C., 1992). However, this effect depends on the relative hydrophilicity of the ionizable monomer compared to the neutral co-monomer. The transition pH can be changed by increasing the hydrophobicity of the gel. As seen in FIG. 1, the hydrogel begins to swell at pH 8, which is below the pKa value of the pendant amine (approx. 10). When the pH inside the gel varies during swelling experiments, the hydrophobicity changes due to a conformational change of the hydrophilic moiety.

Cross-linking density is also important for pH-sensitive swelling, with an increase in cross-linking density reducing the equilibrium degree of swelling. Glucose-sensitive hydrogels (GSHs) containing a fixed amount of GOx (1000 unit/mL) and five different catalase concentrations (0, 100, 300, 600, 900 unit/mL) show identical equilibrium swelling behavior in response to pH changes. The equilibrium data demonstrate that different concentrations of catalase do not influence equilibrium swelling in the HPMA/DMA-based hydrogels with approximately 2 mol % TEGDMA cross-linker.

In insulin delivery and glucose biosensor applications, it is of great practical importance that the GSH respond to glucose concentration changes in the body almost immediately, preferably within 5 minutes. A pH-sensitive hydrogel cannot react to changes in glucose concentration until the pH value inside the hydrogel changes. Once the pH value inside the gel changes, mass transfer of water into or out of the gel will occur. The mass transfer of water is driven by osmotic pressure forces, which in turn are generated by ion exchange processes and polymer conformational changes within the gel. pH-sensitive hydrogels have ionizable groups such as carboxylic acids, tertiary amine groups, and sulfanilamide groups. Ionization of these groups generates strong osmotic pressure forces and swells the gel; deionization of these groups de-swells the gel.

One can drastically decrease the time it takes a species to diffuse into the interior of gel by decreasing the gel thickness and/or increasing the gel porosity. Crosslinking density also affects the response time. Therefore, preferred embodiments are thin and lightly cross-linked hydrogels without macropores, such as those used for the experiment of FIG. 2.

Figure 2:
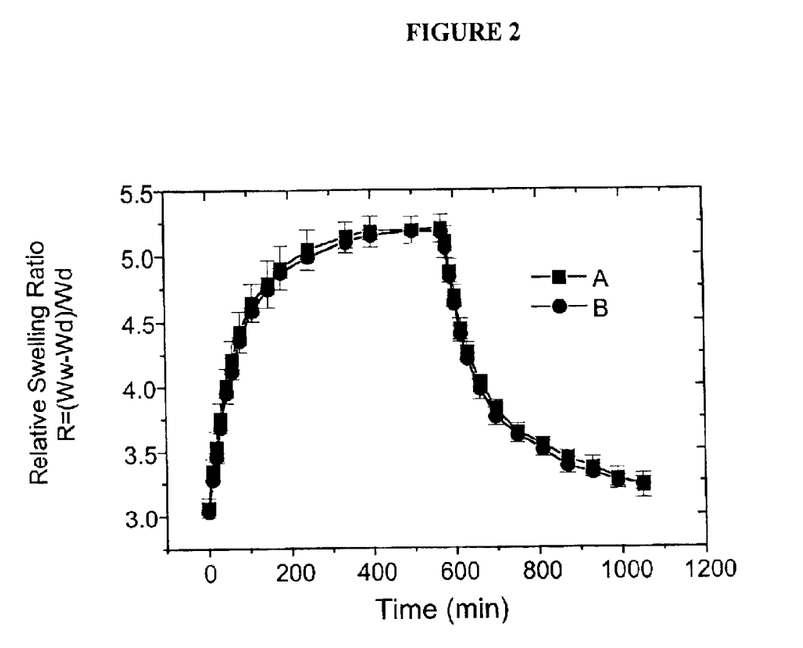
FIG. 2 displays kinetic swelling profiles of a 0.4 mm-thick hydroxypropyl methacrylate/N,N-dimethylaminoethyl methacrylate/tetraethyleneglycol dimethacrylate (HPMA/DMA/TEGDMA) (70:30:2 mol ratio) hydrogel containing a fixed concentration of GOx of 1000 unit/ml (pre-gel solution), with (A) and without (B) catalase. The catalase concentration was 600 unit/ml (pre-gel solution). Measurements were made with the hydrogel immersed in 50 mM Tris buffer at fixed ionic strength of 0.15 M and at room temperature, pH 7.4 and 6.2. Gels in pH 7.4 were switched to pH 6.2 at 0 time and the change in weight measured with a balance. The pH was returned to pH 7.4 at 570 min and the weight again measured with a balance. Relative ratio= (hydrogel weight at a pH—dried hydrogel weight)/dried hydrogel weight. (n=3)

As shown in FIG. 2, the HPMA/DMA-based hydrogels containing GOx and catalase reversibly contract and dilate when the external pH value is cycled. Initially the hydrogel was equilibrated with a pH value of 7.4. At time zero in FIG. 2, the hydrogel was suddenly subjected to a pH value of 6.2, and the swelling was followed as a function of time. After the degree of swelling leveled off, the external pH was switched back to 7.4, and the shrinking (de-swelling) kinetics was observed. Several important points are apparent from FIG. 2. Firstly, the degree of swelling returns to its initial value after the de-swelling is complete; i.e., the swelling process is reversible. Secondly, the swelling and shrinking process is reproducible and identical for various concentrations of catalase (0, 100, 300, and 600 unit/mL) in the GSH. Thus there is no influence of catalase and GOx on the swelling kinetics of the basic hydrogel with 2 mol % cross-linking ratio, at least in the enzyme concentration range studied.

The combined diffusion and reaction processes that occur when a thin (0.4mm) hydrogel, equilibrated with PBS buffer at pH 7.2, is suddenly placed in 100 mL of a glucose solution at concentration 150 mg/dL (FIG. 3), can be described as follows. Glucose diffuses into the GSH, and the enzymatic GOx reaction produces gluconic acid, which ionizes the basic pendant group. This ionization is the driving force for the swelling behavior. Since the reaction is irreversible, it will proceed until all of the glucose in the surrounding solution is converted, which accounts for the long time required to reach equilibrium. Of course in the body, the surrounding glucose is continuously replenished, and a glucose biosensor containing a GSH operates in a steady-state or dynamic equilibrium condition.

Figure 3:
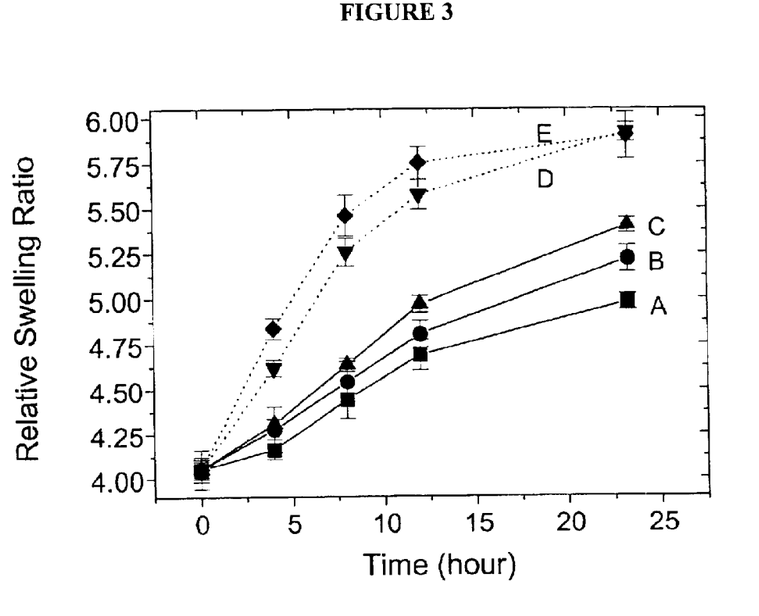
FIG. 3 displays kinetic swelling profiles for the hydroxypropyl methacrylate/N,N-dimethylaminoethyl methacrylate/tetraethyleneglycol dimethacrylate (HPMA/DMA/EGDMA) (70:30:2 mol ratio) hydrogel, with 2 mol % of TEGDMA cross-linker. GOx at a concentration of 1000 unit/ml (pre-gel solution) was co-immobilized with various concentrations of catalase (0, 300, and 600 unit/ml, pre-gel solution). The hydrogels were incubated with PBS (pH 7.2) containing 150 mg/dl glucose at 25 C. One set was performed in air-exposure conditions and a second set performed under conditions of oxygen saturation conditions at 25 C. Curves A,B,C are under air exposure: A is 0 unit catalase/ml; B, 300 unit catalase/ml; C, 600 unit catalase/ml, all for air-exposed conditions. Curves D and E are under oxygen saturated conditions: D is 0 unit catalase/ml, E is 600 unit catalase/ml. (n=3)

Curves A, B, and C of FIG. 3 were measured In these conditions, oxygen is the limiting reactant in the GOx enzymatic pathway. For physiological conditions, the effect of catalase is significant. When the catalase concentration increases from 0, 300, to 600 unit/mL in the GSHs, the relative swelling ratio after 24 h of glucose incubation increases from 4.96±0.042, 5.21±0.072, to 5.44±0.043, at 25° C. The latter value is increased by about 11% when the experiment is performed at 37° C. However, the swelling ratio decreases when the catalase concentration in the GSH is increased from 600 unit/mL to 900 unit/mL, possibly by protein aggregation which denatures the enzyme, or by limiting substrate diffusion. Thus a catalase loading of 600 unit/mL appears to be optimum.

To determine whether catalase inclusion would improve swelling kinetics under oxygen saturation conditions, curves D and E in FIG. 3 were measured with pure oxygen continuously bubbled through the solution. Even under these conditions, the GSHs with co-immobilized catalase show somewhat faster swelling kinetics at earlier times than the GSHs without catalase in several independent experiments. This is probably due to higher local oxygen concentrations inside the hydrogel via the catalase enzymatic reaction. Also, the water production inside GSHs may partially help the fast initial swelling of the GSHs even though oxygen is the major controlling factor in swelling kinetics in our experiments. After 24 h at oxygen saturation, the pH value of the solution surrounding the GSH had dropped from 7.2 to 6.2. By comparing the swelling ratio of curve E in FIG. 3 with FIG. 1, one infers that the pH value inside the hydrogel was also about 6.2.

Figure 4:
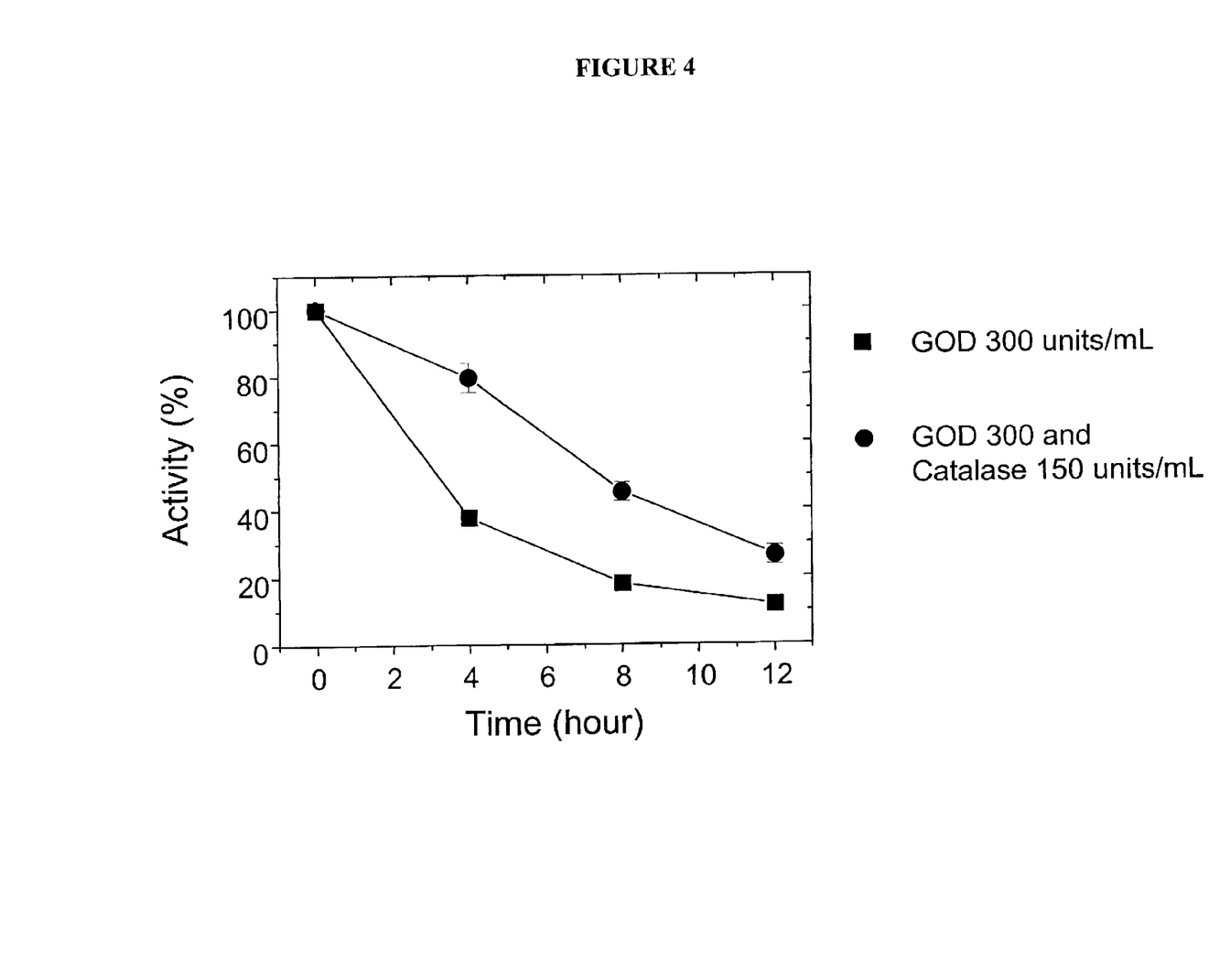
FIG. 4 represents free GOx activity in a hydrogel containing glucose at 500 mg/dl in PBS buffer (pH7.2), measured as a function of time at 25° C. A: 300 unit of GOx/ml; B: 300 unit of GOx/ml and 150 unit of catalase/ml. GOx activities were calculated from the absorbance of GOx enzyme assay, and each point was taken individually at fixed time interval.

The results in FIG. 3 show that the oxygen and the water produced by the catalase reaction increases GOx activity resulting in acceleration of the swelling kinetics. Theoretically, the oxygen requirement of the GOx reaction may be halved by the presence of catalase, provided that both enzymatic reactions are 100% efficient. (Gough DA et al 1988 Anal. Chem., 60:1272; Gough D A et al 1985 Anal. Chem., 57:2351; Klumb L A et al 1992 J. Control. Release 18:59). Catalase may also increase the rate of swelling by reducing peroxide-induced degradation of the GOx enzyme. Our experiments indicate that the activity of free GOx decreases by almost 60% after only four hours of incubation in glucose solutions, and that this decay in activity can be retarded by adding free catalase to the solution (FIG. 4). Since the GOx reaction is irreversible, the final equilibrium degree of swelling should be the same for all of the curves in FIG. 3, provided that oxygen is replenished by dissolution at the air interface. Curves A, B, and C never reach this plateau value. However, if the gel samples corresponding to curves A, B, and C are withdrawn from the glucose solution and placed in pH buffer at 7.2, all three samples take about ten hours to return to the slightly swollen equilibrium state at pH 7.2.

In the experiments of FIGS. 1–4, swelling changes in the pH-sensitive hydrogels were determined by means of the relative weights of the GSHs. In a biosensor, these swelling changes will reflect blood glucose concentration; a type of biosensor pioneered by the present inventor uses a pressure transducer to detect swelling changes (See e.g. U.S. patent application Ser. No. 09/308,392 which is expresly incorporated herein). However, biosensors using similar pH-sensitive GSHs have also been designed using amperometric means to detect blood glucose concentration, incorporation of catalase at these levels confers the same advantage on biosensors using amperometric means (or any other means) to detect glucose concentration, as it does on pressure-transducer biosensors.

The data shown herein demonstrate the effect of the amount of catalase on swelling kinetics by the production of oxygen and water in the thin and lightly-cross linked nonporous GSHS. However, biosensors with a reduced oxygen depletion problem can also be constructed by using catalase together with a semipermeable membrane which permits sufficient diffusion of oxygen and limited diffusion of glucose to the GSHs from exterior fluids such as blood.

As mentioned previously, it is desirable to have a biosensor or drug delivery device that does not include a gas reservoir to enhance the oxygen concentration in the GSH. However, as seen in FIG. 3, catalase substantially enhances the swelling kinetics even under conditions of oxygen saturation. Thus, catalase concentrations in the range studied are also very useful for that type of device.

While the above data and details pertain primarily to glucose oxidase, there are many other embodiments containing different peroxide-generating, analyte-sensitive enzymes. The possibilities include monoamine oxidase as well as most oxidoreductases. The precise optimal concentration range for catalase may vary for different analyte-sensing enzymes, but is easily determined by experiments of the type described herein. Also, while macropore-less, lightly crosslinked gels are most appropriate for hormone-releasing gels and drug delivery devices, for biosensors a higher degree of crosslinking may be feasible.

What is claimed is:

1. A polymer matrix incorporating catalase co-immobilized with an analytic enzyme which generates hydrogen peroxide, wherein the concentration of the catalase in a pregel solution which gels to form the polymer matrix ranges from about 100 units/mL to about 1000 units/mL.

2. The polymer matrix of claim 1, which is pH-sensitive.

3. The polymer matrix of claim 1, which consists of between about 0.5 mol % and about 6 mol % cross-linking monomers.

4. The polymer matrix of claim 1, which when hydrated has a thickness ranging from about 0.1 mm to about 3.0 mm.

5. The polymer matrix of claim 1, wherein the analytic enzyme is glucose oxidase.

6. The polymer matrix of claim 1, wherein the matrix is composed of hydroxypropyl methacrylate, N,N-dimethylaminoethyl methacrylate, and tetraethylenenegly-col dimethacrylate.

7. The polymer matrix of claim 1 in combination with a biosensor in which the polymer matrix is contained, the biosensor including means to monitor and detect changes in the polymer matrix.

8. The polymer matrix-biosensor combination of claim 7, wherein the biosensor is an analyte-responsive drug delivery device, wherein the polymer matrix changes in response to an analyte condition, and wherein the changes in the polymer matrix control the drug delivery from the device.

9. A method of making a polymer matrix containing catalase co-immoblized with an analytic enzyme which generates hydrogen peroxide for use in a biosensor or analyte-responsive drug delivery device, comprising the steps of:

making a pregel solution containing an added analytic enzyme which generates hydrogen peroxide and catalase where the catalase is added at a concentration ranging from about 100 units of catalase/mL pregel solution to about 1000 units catalase/mL pregel solution; and polymerizing the pregel solution to form a polymer matrix and co-immobilize the analytic enzyme with the catalase in the polymer matrix.

10. The method of claim 9, wherein the polymer matrix has between about 0.5 mol % and about 6 mol % cross-linking monomers.

11. The method of claim 10, wherein the polymer matrix is formed to have a thickness when hydrated of between about 0.1 mm and about 3.0 mm.

12. The method of claim 10, wherein the analytic enzyme is glucose oxidase.

* * * * *